United States Patent
Proksa et al.

(10) Patent No.: US 10,813,600 B2
(45) Date of Patent: Oct. 27, 2020

(54) IDENTIFYING TYPES OF ADIPOSE TISSUE

(71) Applicant: KONINKLIJKE PHILIPS N.V., Eindhoven (NL)

(72) Inventors: Roland Proksa, Neu Wulmstorf (DE); Heiner Daerr, Hamburg (DE); Daniela Franz, Munich (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 3 days.

(21) Appl. No.: 16/316,446

(22) PCT Filed: Jul. 13, 2017

(86) PCT No.: PCT/EP2017/067694
§ 371 (c)(1),
(2) Date: Jan. 9, 2019

(87) PCT Pub. No.: WO2018/011340
PCT Pub. Date: Jan. 18, 2018

(65) Prior Publication Data
US 2019/0290222 A1    Sep. 26, 2019

(30) Foreign Application Priority Data
Jul. 15, 2016 (EP) .................................... 16179693

(51) Int. Cl.
*A61B 6/03* (2006.01)
*G06T 7/00* (2017.01)
*A61B 6/00* (2006.01)

(52) U.S. Cl.
CPC ............... *A61B 6/03* (2013.01); *A61B 6/032* (2013.01); *A61B 6/4241* (2013.01); *A61B 6/481* (2013.01); *A61B 6/482* (2013.01); *A61B 6/50* (2013.01); *A61B 6/5211* (2013.01); *G06T 7/0014* (2013.01); *G06T 2207/30004* (2013.01)

(58) Field of Classification Search
CPC ....... A61B 6/032; A61B 6/4241; A61B 6/469; A61B 6/482; A61B 6/463; A61B 6/5211; G06T 7/0012; G06T 2207/10081
See application file for complete search history.

(56) References Cited

U.S. PATENT DOCUMENTS

| | | | |
|---|---|---|---|
| 6,999,549 | B2 | 2/2006 | Sabol |
| 7,526,061 | B2 | 4/2009 | Kobayashi |
| 9,283,317 | B2 | 3/2016 | Lau |
| 2007/0053485 | A1* | 3/2007 | Kobayashi ........... A61B 5/4872 378/19 |

(Continued)

OTHER PUBLICATIONS

Borga et al: "Brown Adipose Tissue in Humans" In: "Methods in Enzymology", Jan. 1, 2014.

(Continued)

*Primary Examiner* — Courtney D Thomas
(74) *Attorney, Agent, or Firm* — Larry Liberchuk (57) ABSTRACT

A method of an image processing apparatus for identifying a type of adipose body tissue within a subject, based on performing a spectral computed tomography (CT) scan of a region of interest of the subject; and using a combination of different image processing techniques to differentiate between at least two adipose tissue types within the region of interest.

18 Claims, 2 Drawing Sheets

(56) References Cited

U.S. PATENT DOCUMENTS

2012/0170826 A1    7/2012  Jang

OTHER PUBLICATIONS

Zachrisson et al: "Soft tissue discrimination ex vivo by dual energy computed tomography", European Journal of Radiology., vol. 75, No. 2, Aug. 1, 2010.
Hünemohr et al: "Tissue decomposition from dual energy CT data for MC based dose calculation in particle therapy", Medical Physics, AIP, Melville, NY, US, vol. 41, No. 6, Jun. 1, 2014.
Fischer et al: "Quantification of Liver Fat in the Presence of Iron and Iodine", Investigative Radiology, vol. 16, No. 6, Jun. 1, 2011.
Cawley et al: "The Medical Care Costs of Obesity: An Instrumental Variables Approach" Journal of Health Economics 31 (2012) 219-230.
Rosenwald et al: "Bi-directional interconversion of brite and white adipocytes", Natrue Cell Biology, Vlo. 15, N. 6, Jun. 2013.
Vegiopoulos et al: "Cyclooxygenase-2 Controls Energy Homeostasis in Mice by de Novo Recruitment of Brown Adipocytes", Science May 28, 2010: vol. 328, Issue 5982, pp. 1158-1161.
Hu et al: "Developments in the imaging of brown adipose tissue and its associations with muscle, puberty, and health in children", Fontriers in Endocrinology, Cellular Endocrinology, Sep. 2011.
Finkelstein et al: "Annual Medical Spending Attributable to Obesity: Payer-And Service-Specific Estimates". Health Affairs, 2009.

\* cited by examiner

IDENTIFYING TYPES OF ADIPOSE TISSUE

CROSS REFERENCE TO RELATED APPLICATIONS

This application is the U.S. National Phase application under 35 U.S.C. § 371 of International Application No. PCT/EP2017/067694, filed Jul. 13, 2017 published as WO 2018/011340 on Jan. 18, 2018, which claims the benefit of European Patent Application Number 16179693.3 filed Jul. 15, 2016. These applications are hereby incorporated by reference herein.

FIELD OF THE INVENTION

The technical field generally relates to identifying types of adipose body tissue, and more particularly to identifying types of adipose body tissue using X-ray computed tomography (CT) scanning.

BACKGROUND OF THE INVENTION

Obesity is a growing worldwide health problem and is a major risk factor for a number of chronic diseases, including diabetes, cardiovascular diseases and cancer. Adipose, or fat, tissue can be divided into two main types with opposed functions: white adipose tissue (WAT) which stores excess energy in the form of lipids, and brown adipose tissue (BAT) which burns lipids and glucose to generate heat in a process called non-shivering thermogenesis. WAT can harbor brown like adipocytes which are called brite (brown-in-white).

Recent studies have demonstrated the bi-directional convertability of brite and white adipocytes in mice. This approach offers a promising means of counteracting obesity by increasing energy expenditure. If the transformation of WAT to brite becomes available for use in humans, it could have a major impact on healthcare and society. In such case, there will be an increased need for monitoring the transformation and this would include imaging techniques.

An imaging technique, called positron emission tomography-computed tomography (PET/CT), offers a currently proposed method for identifying BAT. This technique uses images acquired from both PET and CT devices, which are combined into a single superposed image. Positron emission tomography (PET) is utilized to identify types of adipose tissue based on their uptake of a sugar based radiotracer. Thus, PET imaging is based on metabolic processes. A resulting "functional image", which can be in the form of color-coding the metabolic activity of the scanned organs, e.g. for a particular type of adipose tissue, is superimposed on the "anatomical" CT image to allow simultaneous imaging of body structures and the metabolic activity image of adipose tissue. However, the approach is also somewhat complex and requires two imaging processes.

SUMMARY OF THE INVENTION

Hence, there may be a need to provide an improved and facilitated way of identifying types of adipose body tissue.

The object of the present invention is solved by the subject-matter of the independent claims; wherein further embodiments are incorporated in the dependent claims. It should be noted that the following described aspects of the invention apply also for the image processing apparatus adapted to identify a type of adipose body tissue within a subject, for the system, and for the method as well as for the computer program element and the Computer readable medium.

Methods, image processing apparatus, systems and computer programs are provided for identifying types of adipose body tissue using spectral CT scanning.

In one aspect, a method of identifying a type of adipose body tissue within a subject is provided. The method comprises receiving spectral computed tomography (CT) imaging data of a region of interest of the subject. The method further comprises performing at least one data processing technique on the spectral CT imaging data that differentiates between at least two adipose tissue types within the region of interest based on spectrally different attenuation properties of the at least two adipose tissue types. The method further comprises identifying at least one adipose tissue type from the at least two tissue types.

In another aspect, an image processing apparatus is provided. The image processing apparatus is adapted to identify a type of adipose body tissue within a subject. The apparatus comprises at least one data input interface; and at least one processor. The data input interface is configured to receive spectral computed tomography (CT) imaging data of a region of interest of the subject. The at least one processor is configured to perform at least one data processing technique on the spectral CT imaging data that differentiates between at least two adipose tissue types within the region of interest based on spectrally different attenuation properties of the at least two adipose tissue types. The at least one processor is configured to identify at least one adipose tissue type from the at least two tissue types.

CT scanning is widely used for medical imaging. Conventional standalone CT scanning provides good detail for bone structures and reasonable detail for soft tissues. For example, an abnormal growth like a tumor can be detected. However, it has not heretofore been used for distinguishing between types of adipose tissue.

It is a simpler, quicker and less expensive technique as compared to other forms of imaging such as positron emission tomography (PET) or magnetic resonance imaging (MRI). Also, it provides anatomical information rather than information on biological processes. CT scanning also enables a quantitative analysis to be performed on differentiated tissue types.

By contrast, the current imaging technique, PET-CT, lacks sensitivity and specificity, and is not widely applicable to the general population due to significant radiation exposures and the need to inject a radionuclide tracer. Also, PET-CT can only detect metabolically active BAT that uptakes the injected tracer, which represents only a small percentage of the tissue's total amount in the body. Tracer uptake by metabolically active BAT is sensitive to various factors such as examination room temperature, anesthesia, and the health of the subject during examination. Furthermore, PET-CT measurement involves a binary visual interpretation of a positive or negative depiction of BAT activity by the radiologist. This subjective measure has made systematic comparisons between studies difficult and there is a lack of consensus in the relevant literature.

The present CT solution makes use of spectral CT imaging data and spectrally different attenuation properties of adipose tissue types. For example, BAT/brite tissue has a greater degree of vascularization than WAT tissue, which will thus attenuate X-rays differently at different X-ray energies (or wavelengths), particularly when used in conjunction with contrast enhanced CT data wherein the contrast agent absorbs strongly at an X-ray energy differently from surrounding tissue. Likewise, carbon/oxygen (C/O) ratio is different for BAT/brite tissue as for WAT tissue, which can be determined from attenuation properties at different X-ray energies. These spectral properties can be brought out using spectral processing techniques, i.e. techniques that rely on differentiating based on attenuation at different X-ray energies, that generate data maps for each spectrally dependent property, e.g. a contrast agent map, a C/O ratio map, etc. By using spectral data and spectral processing, different types of adipose tissue can be more clearly differentiated than if non-spectral attenuation information is used (such as a map of attenuation coefficient in Hounsfield units (HU) map).

The differentiation of adipose tissue types may be facilitated by cluster analysis of data points from different maps produced by different processing techniques, as described further below.

Identification of at least one adipose tissue type may comprise classifying data points in the spectral imaging data as corresponding to at least one adipose tissue type, such as BAT, brite and/or WAT. Further, the method may comprise identifying non-fatty soft tissue based on the at least one data processing technique on the spectral CT imaging data that is further able to differentiate at least two adipose two tissue types from each other and to differentiate adipose tissue from non-fatty soft tissue.

The following features are applicable to the method, image processing apparatus and computer program aspects described herein.

The differentiating between at least two adipose tissue types may comprise differentiating based upon vascularization of an adipose tissue type. BAT/brite tissue has greater vascularization density than WAT tissue. Accordingly, at least one data processing technique that allows determination of relative vascularity of tissue allows differentiation of WAT and BAT/brite tissue. Thus, a data processing technique may be applied that determines a quantitative measure of vascularization. For example, a data processing technique may be applied that determines a quantitative measure of contrast agent for determining vascularization.

The CT image scan data may be obtained from a CT scan including introduction of a contrast agent. Such image scan data allows a quantitative measure of vascularization to be determined, since the contrast agent is conducted by the vasculature of the tissue. The spectral (e.g. dual energy) data processing technique may be used to obtain the quantitative measure of vascularization, since the contrast agent will attenuate radiation at specific energies or wavelengths different from other tissue. The spectral (e.g. dual energy) data processing technique may comprise processing the image scan data filtered at different wavelengths or frequencies.

The differentiating between at least two adipose tissue types may comprise differentiating based upon selective imaging of the contrast agent by K shell binding energies. Such K-edge imaging provides a clear differentiation between vascular and other tissue when spectral imaging is utilized in combination with spectral data processing, thereby allowing a quantitative measure of vascularization to be obtained.

The differentiating between at least two adipose tissue types may comprise differentiating based upon the lipid content of tissue in the region of interest. From this, fatty or adipose tissue is able to be distinguished from other types of tissue, e.g. non-fatty soft tissue. The lipid content will have an effect on spectral attenuation properties, which can be picked up and identified by spectral imaging and processing.

The differentiating based upon the lipid content may comprise determining at least one of the carbon/oxygen ratio of the adipose tissue and Compton and photo effect ratio, both of which are indicative of tissue having high lipid content (i.e. adipose tissue). Thus, a data processing technique may be applied to determine a quantitative measure of at least one of carbon and oxygen ratio and Compton and photo effect ratio in the tissue. Adipose tissue has a high carbon and oxygen ratio and high Compton and photo effect ratio as compared to other types of tissue, thereby allowing fatty tissue to be differentiated from other types of tissue. These ratios can be determined based on different X-ray attenuation properties at different X-ray energies, which can be processed to produce a data map of one or both of the ratios.

The differentiating the at least two types of adipose tissue may be based on intensity of attenuation. Intensity of attenuation may be determined from a non-spectrally based data processing technique. WAT and BAT/brite exhibit different intensity of attenuation of CT image data from each other and from that of other non-fatty tissue, thereby allowing differentiation of adipose tissue from non-fatty tissue and adipose tissue types. Intensity of attenuation may be determined from a conventional HU map.

The at least one processor may be configured to perform at least one data processing technique that differentiates adipose tissue types based on spectrally selective attenuation of a biomarker of the at least two adipose tissue types.

The at least one processor may be configured to perform a data processing technique on the spectral CT imaging data to determine a data map of a variable representing any one or more of a quantity of attenuation, a quantity of lipid content, a quantity of vascularization such as a quantity of contrast agent.

The at least one processor may be configured to perform a combination of different data processing techniques on the spectral CT imaging data that respectively represent the spectral CT imaging data in different variable spaces, wherein results of the different data processing techniques in the different variable spaces differentiate the at least two adipose tissue types. A combination of data processing techniques in different variable spaces allows an increase in the probability of correctly identifying an adipose tissue type. For example, a combination of two or more of the following data processing techniques could be utilized: a data processing technique based upon determining vascularization (with the variable space being a quantitative measure of vascularization), a data processing technique based upon determining carbon to oxygen ratio (with the variable space being a quantitative measure of oxygen and carbon ratio), and a data processing technique based on intensity of attenuation (with the variable space being a quantitative measure of intensity of attenuation).

The differentiating may comprise performing a combination of the following data processing techniques on the CT scan image data in the region of interest in order to differentiate adipose tissue types: intensity of attenuation based data processing, carbon oxygen ratio data processing and data processing to determine density of vascularization. These data processing techniques allow accurate differentiation of adipose tissue types.

The at least one processor may be configured to identify at least one adipose tissue type based on a combination of different data maps obtained by data processing techniques performed on the spectral CT imaging data. The at least one processor may be configured to perform data processing techniques on the spectral CT imaging data to determine at least two of the following different data maps a quantity of lipid content, a quantity of contrast agent; and a quantity of attenuation. The at least one processor may be configured to perform data processing techniques on the spectral CT scan image data to determine the following different data maps a quantity of lipid content, a quantity of contrast agent, and a quantity of attenuation.

The at least one processor may be configured to determine a quantitative measure of the at least one identified adipose tissue type. The quantitative measure may be indicative of at least one of: white adipose tissue, WAT, fraction of tissue in the region of interest, BAT/brite adipose tissue fraction of tissue in the region of interest, total adipose tissue fraction of tissue in the region of interest, BAT/brite to WAT fraction, perfusion of BAT/brite tissue and thermogenic activity, lipid content of BAT/brite tissue and thermogenic status of BAT/brite tissue. Determining the quantitative measure may comprise a counting operation on a number of data points identified for each tissue type.

The identifying may comprise associating, by a computer-implemented data processing technique, data points of the CT scan image data with a type of adipose tissue (e.g. WAT or BAT/brite) or a probability of the data points being the associated type of adipose tissue. Based on the associating, the method or processor may quantify the at least two types of adipose tissue. The associating may be performed on a basis of clusters of data points established by differentiating using the at least one data processing technique. The data points may be pixels, with the pixels being determined by a resolution of the CT scan image data. Such a cluster based approach allows the data processing technique to readily differentiate data points.

The differentiating of at least two adipose tissue types may comprise performing a cluster analysis on the CT scan image data in a three dimensional space of intensity of attenuation, carbon oxygen ratio and degree of vascularization or a two dimensional space of any two of intensity of attenuation, carbon oxygen ratio and degree of vascularization. These specific variable spaces enable a strong probability of accurate identification of particular clusters as belonging to an adipose tissue type. The cluster analysis allows a further step of associating a cluster with an adipose tissue type to perform the identifying step.

The at least one processor may be configured to perform cluster analysis on the data maps to place data points in a plural dimensional space of the map quantities; and to identify different clusters of data points based on the cluster analysis corresponding to different types of adipose tissue. The at least one processor may be configured to determine a quantitative measure of the types of adipose tissue based on the identified different clusters.

The method may comprise outputting to a user interface the identified adipose tissue type. For example, the method may comprise displaying an image of the CT scan image data with visually identifiable adipose tissue type portions imaged thereon, such as by way of different colors for different tissue types, e.g. different colors for adipose tissue and other soft tissue and/or different colors for WAT adipose tissue and BAT/brite tissue. Additionally, or alternatively, a numerical analysis concerning the adipose tissue types may be output. The at least one processor may be configured to generate at least one image for display that includes visually differentiable adipose tissue types superimposed on a CT image corresponding to the spectral CT imaging data.

The method may comprise the step of performing a CT scan to obtain the CT scan image data.

The method may include the step of performing activation of brown adipose tissue (BAT)/brite adipose tissue prior to scanning Activated BAT/brite shows a higher vascularization compared to non-activated BAT/brite. The difference in vascularization can be applied as a further identifier for BAT/brite and additionally as a quantitative measure of the activity. The step of performing activation of BAT may comprises cooling at least the region of interest of the subject for a period of time.

A computer program stored on memory is also provided, which is adapted to perform the features described above.

A system for identifying a type of adipose body tissue within a subject is also provided, which comprises the image processing apparatus above and a CT scanner to obtain the CT scan image data.

These and other aspects of the invention will be apparent from and elucidated with reference to the embodiment(s) described hereinafter.

DESCRIPTION OF THE DRAWINGS

The exemplary embodiments will hereinafter be described in conjunction with the following drawing figures, wherein like numerals denote like elements, and wherein.

DETAILED DESCRIPTION OF THE EMBODIMENTS

The following detailed description is merely exemplary in nature and is not intended to limit the application and uses. Furthermore, there is no intention to be bound by any expressed or implied theory presented in the preceding technical field, background, brief summary or the following detailed description.

Figure 1:
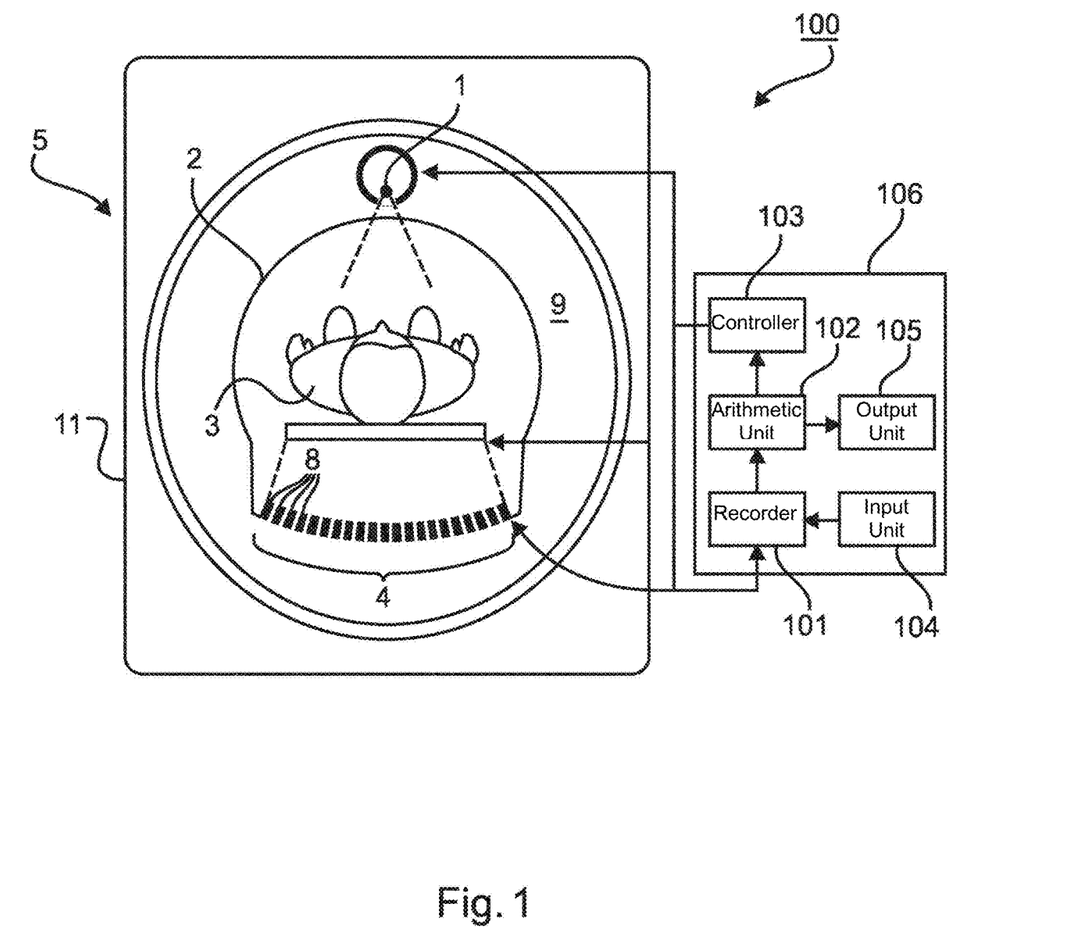
FIG. 1 is a schematic view of a CT scanning device in accordance with an embodiment.

FIG. 1 is a view representing the structure of an X-ray CT device 100 according to the embodiment seen from the axial direction. The CT device 100 comprises a CT scanner 5 and an image processing apparatus 106. An aperture 2 is formed in the center of a gantry 9 of the CT scanner 5 of the X-ray CT device 100, which allows entry of a subject 3. The CT scanner 5 of the X-ray CT device 100 is provided with an X-ray emitter 1 and an X-ray detector 4, both of which are rotatably supported with the gantry 9 relative to a housing 11, with the center of the aperture 2 being the rotary center axis. This allows rotational imaging of the subject 3 in the aperture 2. The X-ray detector 4 is disposed opposite the X-ray emitter 1 having the subject 3 interposed therebetween. The X-ray detector 4 is divided into a plurality of detector modules 8 to detect radiation within the range of the emitter 1.

The control of imaging of the subject 3 in the X-ray CT device 100 for data collection is carried out by a controller 103, by a recorder 101 and an arithmetic unit 102 based on the scan condition set by the user via an input unit 104. Multiple projection data derived from the data collection sections 1, 4 during the rotational imaging are recorded in the recorder 101. Then arithmetic unit 102 carries out arithmetic image processing so that an output unit 105 can display such information as a tomographic image of the subject 3.

Figure 2:
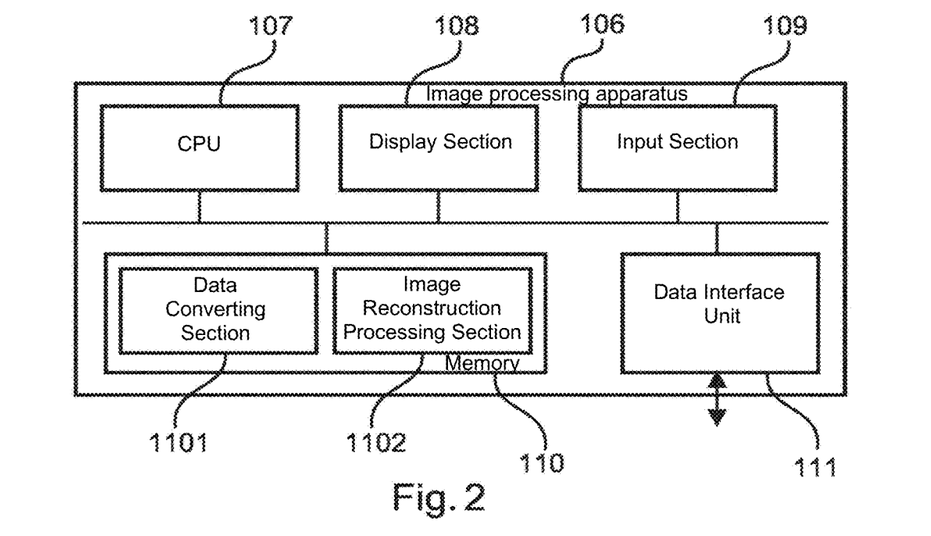
FIG. 2 is a block diagram of an imaging control section of the X-ray CT device of FIG. 1.

Referring additionally to the block diagram shown in FIG. 1, an image processing apparatus 106 of the X-ray CT device 100 may include the recorder 101, the arithmetic unit 102, the controller 103, the input unit 104, and the output unit 105. The image processing apparatus 106 may be configured as a computer having an inner bus connecting at least one processor such as Central Processing Unit (CPU) 107 and a storage section including the memory 110, which may include a non-transitory memory such as a hard disk drive (HDD) for storing various types of computer processing programs such as a data converting section 1101, an image reconstruction processing section 1102 and a program for identifying a type of adipose body tissue within a subject as detailed further herein, which are executed by the CPU 107. The inner bus may further connect to a display section 108 for displaying images such as via the output unit 105, an input section 109 such as a keyboard, touchscreen and/or a mouse and a data interface unit 111 to which the projection data are input.

In the present exemplary embodiment, the image processing apparatus 106 is integrated with the X-ray CT device 100. However, it could be a standalone image processing apparatus 106 including a data input interface 111 for receiving CT scan image data over a wired or wireless connection, via a memory device or otherwise.

The at least one processor of the image processing apparatus 106 described herein may be implemented by the central processing unit 107. Alternatively, one or more distributed image processors (not shown) may be provided that have access to image data obtained by the CT device 100 and one or more memories, such as the memory 110 described above, storing instructions for implementing the image processing methods/techniques described herein. The memory 110 may be of a permanent or transient kind. The memory 110 may also be used to store the CT scan image data obtained by the CT device 100.

The central processing unit 107 is adapted to perform at least one data processing technique on the spectral CT imaging data that differentiates between at least two adipose tissue types within the region of interest based on spectrally different attenuation properties of the at least two adipose tissue types: for example, WAT and BAT. Conventional CT scanning provides a quantitative measure of intensity of attenuation by body tissue, known as the Hounsfield scale. The image processing techniques described below a manner by which CT scan image data obtained from a known CT scanning device 100 can reliably be used for identifying adipose tissue types.

The following facts concerning adipose tissue are of relevance to establishing a way to identify a type of adipose tissue using CT image scan data.

WAT functions to store fat and consists of cells with large intracellular lipid droplets. It therefore has a relatively high lipid content. The carbon to oxygen ratio (C—O-ratio) in lipid is substantially different from other soft biological tissue.

In contrast to WAT adipocytes, brown adipocytes are further characterized by multiple smaller intracellular lipid droplets, have lower lipid content by volume, and greater intracellular water.

Figure 3:
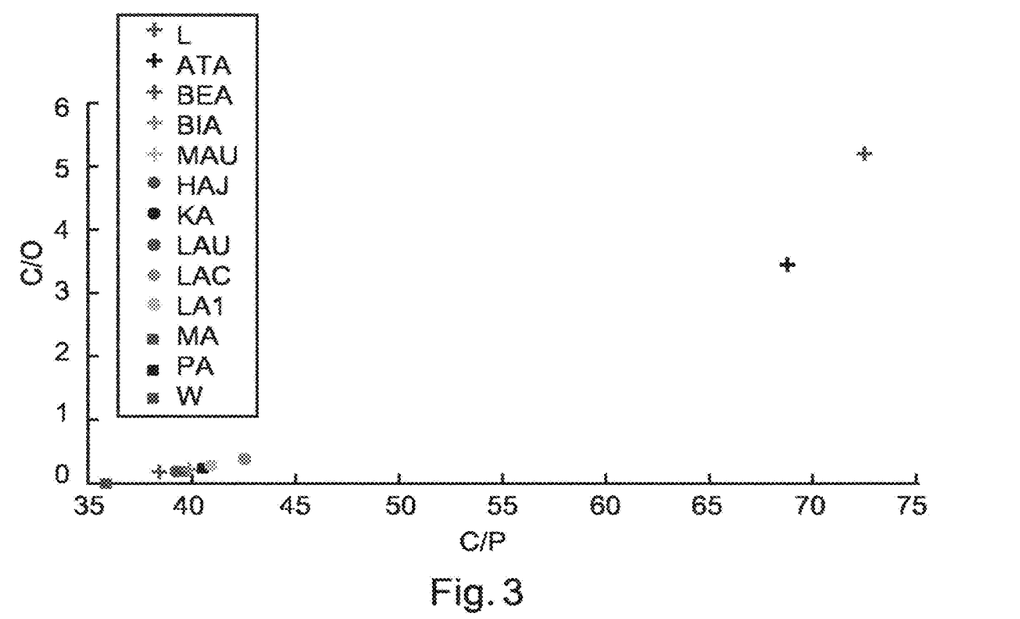
FIG. 3 is a scatter plot of the Compton to photo effect ratio against the C/O ratio for various tissue types.

Nonetheless, adipose tissue of both kinds have relatively large lipid content, and thus carbon to oxygen ratio, as compared other non-fatty soft tissue. To demonstrate these facts, FIG. 3 shows a scatter plot of the Compton to photo effect ratio against the C/O ratio for various tissue types. There is a monotone functional relation-ship between the C/O ratio and the Compton to photo effect ratio. Adipose tissue has a C/O ratio well above 1 while other soft tissue types have a C/O ratio below 1. Additionally, adipose tissue can be identified by its higher Compton/Photo effect ratio (being well above 50) compared to other soft tissues (below 50). The amount of Compton and photo effect can be applied to identify adipose tissue types.

BAT and brite is highly vascularized while WAT is not.

In one embodiment, the CT device 100 is adapted to perform a dual energy or other spectral CT scan. As such, the CT image scan data obtained therefrom, and available to be received by the at least one processor 107, is of the dual energy or spectral variety. Spectral energy CT utilizes the different attenuation properties of matter at different energy levels. A lower energy level is associated with an increase in photoelectric interactions especially in substances with higher atomic number such as iodine and calcium. The attenuation value at different energies within a voxel can subsequently be analyzed using material decomposition techniques and post processing of images can provide additional diagnostic value compared to single energy conventional CT. In particular, the energy levels can be selected so that one is strongly attenuated by a contrast agent used in the CT scanning process, thereby allowing a quantitative measure of vascularization to be determined. One example spectral energy CT scan is known as K-edge CT imaging and is particularly suitable for differentiating vascular tissue through the vehicle of a suitable contrast agent in the vasculature. K-edge imaging results in a particularly strong attenuation of CT radiation at specific wavelengths due to K-shell electron transitions.

In one embodiment, the following method is used to identify adipose tissue.

The subject 3 is injected with a contrast agent, such as iodine, prior to scanning. This assists in showing the degree of vascularization of the tissue. The subject then enters the aperture 2 of the CT device 100 and spectral energy scanning is performed. The collected CT scan image data is then processed and then tomographic maps are generated from the processed data.

The image processing method described herein may be carried out separately from the CT device 100. Thus, the image scan data, which has been obtained by spectral energy CT scanning and from a contrast agent injected body, is received by at least one processor 107 for image processing to identify adipose tissue.

In the image scan data, a region of interest is identified. The region of interest may be defined by an operator and through a user interface device 104 such as a touchscreen device, a mouse, a keyboard, etc. Alternatively, the region of interest can be algorithmically identified by the at least one processor 107, such as the CPU 107.

In one embodiment, three data processing techniques for differentiating adipose tissue can be carried out on the CT scan image data in the region of interest, and a map generated for each analysis. The data processing techniques correspond to material decomposition techniques on the acquired imaging data to generate different maps. The first type of analysis is a conventional CT attenuation approach, which differentiates tissue type by its Hounsfield units (HU) of radiodensity or intensity of attenuation. A HU map of radiodensity is generated by the first data processing technique. The second is a measure of tissue vascularization and represented by a contrast agent (CA) map. The third analysis is an assessment of the lipid content of the tissue, such as the C—O-ratio to generate a C—O-ratio map. The following maps of data can thus be provided: a CT map, a HU map and a C—O-ratio map. It is envisaged that one or more further or replacement data maps could be provided. For example, a Compton and photo ratio map could be added or used in place of the C—O-ratio map. Further data maps, provided they represent a different variable able to further differentiate adipose tissue types as compared to the other maps, could allow increased clarity of differentiation and identification of adipose tissue types.

The second and third data processing techniques (exemplified by producing CA and CO ratio maps) process spectral components of each data point to differentiate tissue types. That is, each data point comprises plural measurements at different X-ray energy levels. Based on attenuation of X-rays at certain energy levels, the data can be transformed into one or maps of spectrally differentiating properties.

For the CA map, K-edge imaging can be applied to generate the map. K-edge is the binding energy of the K shell electron of an atom. There is a sudden increase in the attenuation coefficient of photons occurring at a photon energy just above the binding energy of the K shell electron of the atoms interacting with the photons. This sudden increase in attenuation is due to photoelectric absorption of the photons. X-ray contrast agents, such as iodine, have ideal K shell binding energies for the absorption of X-rays.

A three-dimensional feature space is defined for the quantities of the three maps. That is, a three-dimensional space of a quantitative measure of contrast agent representing vascularization, a quantitative measure of intensity of attenuation, and a quantitative measure of carbon to oxygen ratio is established for each data point (pixel) in the region of interest of the CT scan image data. A cluster analysis is then performed for the data points in the three-dimensional variable space to classify or identify tissue as being one of: non-fatty soft tissue (st), wat and bat/brite. This clustering is based on the physiological properties of the tissue and an indication of tissue features is given in the table below. The outcome of the cluster analysis can be based on either a likelihood that a specific value belongs to a classification component or a discrete assignment to one of the components. The image processing techniques have been selected to provide data with respect to variables for each data point, where the variables are able to suitably cluster data to differentiate at least WAT and BAT/brite tissue types, thereby facilitating subsequent algorithmic classification/identification of the tissue types.

The cluster analysis may be algorithmically performed to identify each cluster in combination with a priori knowledge of a likely location of a cluster for a particular type of adipose tissue within the three-dimensional variable space.

|  | CA | HU | Lipid |
| --- | --- | --- | --- |
| ST | Higher than WAT | 0-150 | 0.05-0.25 |
| WAT | Low | −100 ... −50 | ~2.0 |
| BAT/brite | Higher than WAT | Higher than WAT | Lower than WAT |

As evident from the above table, WAT can be readily differentiated from BAT in the CA map as being low contrast tissue (low level of vascularization). Also, the lipid (carbon and oxygen ration) differentiates WAT from BAT by its relatively high lipid content and is also able to differentiate adipose tissue (WAT and BAT/brite) from other non-fatty tissue (ST). Further, the intensity of attenuation map differentiates WAT from BAT/brite. Whilst these image processing techniques may not be sufficient independently to sufficiently surely differentiate WAT and BAT/brite from each other and from other non-fatty tissue (ST), the combination of at least two of these techniques increases the likelihood of a correct differentiation and identification of adipose tissue type.

One possible result of the classification of ST, BAT and WAT can be used to generate images for display on the display section 108 that allow a viewer to visually identify the different types of tissue such as by use of coloring. Further, the indication of the different types of tissue can be superimposed on the CT scan to allow the viewer to locate in the human body the tissue types. The images may show the anatomical distribution of the adipose tissue.

Additionally, or alternatively, the method may comprise a quantitative analysis to quantify WAT, BAT/brite and/or ST tissue. For quantitative assessment, various quantities can be numerically determined which are useful indicators of the relevant properties. The table below presents a number of these quantities and of what they are indicative. In the table, x refers to a data point and n is the number of image points in the region of interest (ROI).

| Quantity | Indicative of |
| --- | --- |
| $\sum_{x \in ROI} \frac{WAT(x)}{n}$ | white adipose tissue fraction |
| $\sum_{x \in ROI} \frac{BAT(x)}{n}$ | Brown/brite adipose tissue fraction |
| $\sum_{x \in ROI} \frac{WAT(x) + BAT(x)}{n}$ | total adipose tissue fraction |
| $\frac{\sum_{x \in ROI} WAT(x)}{\sum_{x \in ROI} BAT(x)}$ | the BAT/brite to WAT fraction |
| $\sum_{x \in ROI} \frac{BAT(x)CA(x)}{n}$ | perfusion of the BAT/brite and the thermogenic activity |
| $\sum_{x \in ROI} \frac{BAT(x)L(x)}{n}$ | lipid content of the BAT/brite and the thermogenic status of BAT/brite |

In an alternative embodiment, the CT device 100 may not generate the images. For example, the CT device 100 may only output numerical results as described above.

In another alternative embodiment, the CT device 100 may not perform the three analyses. For example, only the CA, or only the lipid analysis, could be used for differentiating WAT and BAT tissue or any two or more of the image processing techniques described herein may be performed.

Returning to the present embodiment, the method can include steps for improving the classification of the tissue components.

As an example of this, a priori knowledge may be used. The WAT map can undergo a model based segmentation and registration process to incorporate anatomical knowledge of adipose tissue. False positive and false negative results of the classification can be reduced based on the segmentation results.

It is known that BAT occurs within or next to WAT and is usually located directly under the skin. Also, morphologically, BAT cells are clustered to a larger region. This information can guide the CPU 107 in adipose tissue identification.

Another possible step for improving the classification is to differentiate tissue by its Compton to photo effect ratio, as described above with respect to FIG. 3.

Another possible step for improving the classification is to carry out BAT/brite activation prior to scanning BAT/brite can be activated by cooling the subject 3 for a period of time (typically about 30 minutes). It is known that activated BAT/brite shows a higher vascularization compared to non-activated BAT/brite. Also, there may be a decrease in the lipid content of BAT/brite during activation.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the disclosure in any way. Rather, the foregoing detailed description will provide those skilled in the art with a convenient road map for implementing the exemplary embodiment or exemplary embodiments. It should be understood that various changes can be made in the function and arrangement of elements without departing from the scope of the disclosure as set forth in the appended claims and the legal equivalents thereof.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An image processing apparatus adapted to identify a type of adipose body tissue within a subject, the apparatus comprising:
   at least one data input interface; and
   at least one processors circuitry;
   wherein the data input interface is configured to receive spectral computed tomography (CT) imaging data of a region of interest of the subject; and
   wherein the at least one processor circuitry is configured to:
      perform at least one data processing technique on the spectral CT imaging data that differentiates between at least two adipose tissue types within the region of interest based on spectrally different attenuation properties of the at least two adipose tissue types; and
      identify at least one adipose tissue type from the at least two tissue types.

2. The image processing apparatus of claim 1, wherein the at least one data processing technique includes a data processing technique that differentiates between at least two adipose tissue types based upon differing vascularization of one of the adipose tissue types.

3. The image processing apparatus of claim 1, wherein the spectral CT imaging data is contrast enhanced spectral CT imaging data.

4. The image processing apparatus of claim 1, wherein the at least one data processing technique includes a data processing technique that differentiates between at least two adipose tissue types based upon selective imaging of a contrast agent by differing K shell binding energies.

5. The image processing apparatus of claim 1, wherein the at least one data processing technique includes a data processing technique that differentiates between at least two adipose tissue types based upon the lipid content of tissue in the region of interest.

6. The image processing apparatus of claim 1, wherein the at least one data processing technique includes a data processing technique that differentiates based upon the carbon/oxygen ratio of the adipose tissue.

7. The image processing apparatus of claim 1, wherein the at least one processor circuitry is configured to perform a data processing technique that differentiates the at least two types of adipose tissue based on intensity of attenuation.

8. The image processing apparatus of claim 1, wherein the at least one processor circuitry is configured to perform a combination of different data processing techniques on the spectral CT imaging data that respectively represent the spectral CT imaging data in different variable spaces, wherein results of the different data processing techniques in the different variable spaces differentiate the at least two adipose tissue types.

9. The image processing apparatus of claim 1, wherein the at least one processor circuitry is configured determine a quantitative measure of the at least one identified adipose tissue type.

10. The image processing apparatus of claim 1, wherein the at least one processor circuitry is configured to perform data processing techniques on the spectral CT imaging data to determine at least two of the following different data maps:
a quantity of lipid content;
a quantity of contrast agent; and
a quantity of attenuation.

11. The image processing apparatus of claim 1, wherein the at least one processor circuitry is configured to:
perform cluster analysis on data maps to place data points in a plural dimensional space of the map quantities; and
identify different clusters of data points based on the cluster analysis corresponding to different types of adipose tissue.

12. A system for identifying a type of adipose body tissue within a subject, comprising:
an image processing apparatus adapted to identify a type of adipose body tissue within a subject, the apparatus comprising:
at least one data input interface; and
at least one processor circuitry;
wherein the data input interface is configured to receive spectral computed tomography (CT) imaging data of a region of interest of the subject; and
wherein the at least one processor circuitry is configured to:
perform at least one data processing technique on the spectral CT imaging data that differentiates between at least two adipose tissue types within the region of interest based on spectrally different attenuation properties of the at least two adipose tissue types; and
identify at least one adipose tissue type from the at least two tissue types; and
a spectral CT scanner to obtain the spectral CT imaging data.

13. The system of claim 12, wherein the at least one processor circuitry is configured to perform data processing techniques on the spectral CT imaging data to determine at least two of the following different data maps:
a quantity of lipid content;
a quantity of contrast agent; and
a quantity of attenuation.

14. The system of claim 12, wherein the at least one processor circuitry is configured to:
perform cluster analysis on data maps to place data points in a plural dimensional space of the map quantities; and
identify different clusters of data points based on the cluster analysis corresponding to different types of adipose tissue.

15. A method of identifying a type of adipose body tissue within a subject, the method comprising:
receiving spectral computed tomography (CT) imaging data of a region of interest of the subject;
performing at least one data processing technique on the spectral CT imaging data that differentiates between at least two adipose tissue types within the region of interest based on spectrally different attenuation properties of the at least two adipose tissue types; and
identifying at least one adipose tissue type from the at least two tissue types.

16. A non-transitory computer readable medium having stored a program element for controlling an apparatus, which, when being executed by processor circuitry, the apparatus is configured to perform the method according to claim 15.

17. The method of claim 15, further comprising:
performing data processing techniques on the spectral CT imaging data to determine at least two of the following different data maps:
a quantity of lipid content;
a quantity of contrast agent; and
a quantity of attenuation.

18. The method of claim 15, further comprising:
performing cluster analysis on data maps to place data points in a plural dimensional space of the map quantities; and
identifying different clusters of data points based on the cluster analysis corresponding to different types of adipose tissue.

* * * * *